United States Patent [19]

Chester et al.

[11] 4,387,261

[45] Jun. 7, 1983

[54] TREATMENT OF EFFLUENT RESULTING FROM CONVERSION OF METHANOL TO GASOLINE IN ORDER TO DECREASE DURENE AND PRODUCE DISTILLATE

[75] Inventors: Arthur W. Chester; Yung F. Chu, both of Cherry Hill, N.J.

[73] Assignee: Mobil Oil Corporation, New York, N.Y.

[21] Appl. No.: 366,949

[22] Filed: Apr. 9, 1982

[51] Int. Cl.³ .......................... C07C 3/58; C07C 1/04; C07C 1/16; C07C 1/22
[52] U.S. Cl. .................................... 585/489; 585/408; 585/412; 585/419; 585/469; 585/483; 208/66
[58] Field of Search ............... 585/408, 412, 413, 419, 585/469, 483, 488, 489; 208/66

[56] References Cited

U.S. PATENT DOCUMENTS

| | | | |
|---|---|---|---|
| 3,945,913 | 3/1976 | Brennan et al. | 585/489 |
| 4,035,430 | 7/1977 | Dwyer et al. | 585/322 |
| 4,304,951 | 12/1981 | Garwood et al. | 585/469 |
| 4,347,397 | 8/1982 | Dwyer et al. | 585/469 |

FOREIGN PATENT DOCUMENTS 1497172  1/1978  United Kingdom ............... 585/476

Primary Examiner—Delbert E. Gantz
Assistant Examiner—A. Pal
Attorney, Agent, or Firm—Charles A. Huggett; Charles J. Speciale; L. G. Wise

[57] ABSTRACT

A process is disclosed for the dealkylation of durene resulting from a methanol to gasoline conversion by contacting a durene-containing fraction with zeolite ZSM-12 at elevated temperatures and pressures.

5 Claims, No Drawings

TREATMENT OF EFFLUENT RESULTING FROM CONVERSION OF METHANOL TO GASOLINE IN ORDER TO DECREASE DURENE AND PRODUCE DISTILLATE

BACKGROUND OF THE INVENTION

This invention relates generally to the conversion of methanol so as to produce gasoline and, more particularly, to the treatment of all or a portion of the effluent obtained from said conversion process in order to decrease durene.

CROSS REFERENCE TO RELATED APPLICATIONS

This application is related to application Ser. No. 257,693, filed Apr. 27, 1981 now U.S. Pat. No. 4,347,397, and application Ser. No. 225,061, filed Jan. 14, 1981 now U.S. Pat. No. 4,304,951.

DESCRIPTION OF PRIOR ART

The conversion of methanol to gasoline is an important area of technology which has the potential of becoming even more important as the supply of crude oil is diminished and/or increased in price. Particularly advantageous catalysts which are utilized in the conversion of methanol to gasoline are a special class of crystalline aluminosilicate zeolite catalysts of which HZSM-5 is the most preferred member. There are many patents and publications which describe the conversion of methanol to gasoline over said special zeolites, including U.S. Pat. Nos. 3,931,349; 3,969,426; 3,899,544; 3,894,104; 3,904,916; 3,894,102; the disclosures of which are incorporated by reference.

One particular problem residing in the conversion of methanol to gasoline over ZSM-5 type zeolites is that durene is produced in amounts higher than that expected from $C_{10}$ aromatic equilibrium distributions. Once an aromatic ring is formed in the presence of unreacted methanol, alkylation to tetramethylbenzenes occurs rapidly, but the smaller higher melting durene molecule (1,2,4,5-tetramethylbenzene, melting point 175°) diffuses out of the ZSM-5 pore much more rapidly than isodurene (1,2,3,5-tetramethylbenzene) or prehnitene (1,2,3,4-tetramethylbenzene). There have been various proposals advanced in order to control or minimize the amount of durene which is produced in the catalytic conversion of methanol to gasoline.

The proposals for durene reduction have generally fallen into two broad categories. One approach to the problem has been to vary the reaction conditions regarding the conversion of methanol such that durene is not formed at all or formed in small amounts. Approaches of this type are represented by U.S. Pat. No. 4,025,576 wherein it is stated that durene formation is less in the conversion of methanol if methanol is first converted to olefins and the olefins thereafter converted to gasoline.

The second approach with regard to durene control was not to attempt to control the amount of durene which was formed in the methanol to gasoline reaction but to process the durene so formed in order to diminish it. It is in this latter area that the novel process of this invention is operative and it represents an improvement over the heretofore practiced teachings of the prior art.

In this connection, U.S. Pat. No. 3,969,426 is concerned with a process for the diminishing of durene produced in a methanol to gasoline process by reacting a durene-containing stream with low boiling aromatics such as benzene and toluene in order to transalkylate and thereby diminish the durene content.

In like manner, aforementioned applications Ser. Nos. 257,693 and 225,061 are concerned with processes for treating all or a portion of the effluent resulting from the conversion of methanol to gasoline in order to decrease durene either by contacting the same with an isomerization catalyst or a hydrogenation catalyst.

There are other patents dealing with durene such as U.S. Pat. No. 4,067,827 which teaches high selectivity transalkylation of alkyl aromatic compounds including durene with a wide variety of catalysts, including ZSM-5, ZSM-11, ZSM-12, etc.

U.S. Pat. No. 4,098,836 also teaches an improved process for the vapor phase isomerization of various aromatic compounds, including durene with catalysts including ZSM-5, ZSM-11, ZSM-35, and ZSM-12.

U.S. Pat. Nos. 4,158,676 and 4,159,283 deal with isomerization processes of a feed containing ethylbenzene and an alkyl aromatic compound which can be durene with a wide variety of crystalline aluminosilicate zeolites, including ZSM-12.

The novel process of this invention represents an improvement over the teachings of the above-identified United States patents and pending applications in that it is directed towards the dealkylation of a durene-containing fraction consisting essentially of $C_9+$ aromatics under rather severe conditions and is in no way concerned with an isomerization process or a transalkylation process or a disproportionation process. Thus, the object of this invention is to contact a durene-containing fraction with a particular zeolite; namely, ZSM-12, under conditions such that the durene fraction is dealkylated to a lower melting or boiling product.

DESCRIPTION OF THE PREFERRED EMBODIMENT

The novel process of this invention is concerned with treatment of either the total effluent from a methanol to gasoline process or a durene-containing bottoms fraction (obtained from the total gasoline fraction by topping off at least a light olefinic fraction) by dealkylation of the same at elevated temperatures and pressures over a crystalline aluminosilicate zeolite identified as ZSM-12.

Zeolite ZSM-12 is a known zeolite which is described in U.S. Pat. No. 3,832,449, the disclosure of which is incorporated by reference. The novel process of this invention is carried out simply by contacting a durene-containing bottoms fraction from a methanol to gasoline synthesis with zeolite ZSM-12, preferably having incorporated therewith a hydrogenation/dehydrogenation component such as platinum at pressures greater than 250 psig, i.e. 250–1000 psig, temperatures with a range of 800°–1050° F. and at a weight hourly space velocity of 0.5–10 and a hydrogen to hydrocarbon ratio greater than 1 and preferably 1–5.

In this connection, it is to be noted that the conditions of the instant application differ from aforementioned copending Ser. No. 257,693 with regard to the operating conditions, i.e. temperature, pressure, space velocity and in the fact that hydrogen is required.

The reason for the different conditions is due to the fact that an entirely different reaction is taking place in the instant application than that which is involved in Ser. No. 257,693, i.e. dealkylation as opposed to isomerization. In this connection, the examples of said copending application clearly show that the durene is primarily isomerized aromatic isomers, primarily 1,2,3,5- and 1,2,3,4-tetramethylbenzenes. The novel process of this invention is concerned with the dealkylation of durene in high amounts, i.e. conversions as high as 80%, with a product loss, i.e. to $C_1-C_4$s of about 15-25%, but at a substantial yield increase of benzene, toluene and xylenes (BTX). It has been found that the dealkylation of durene is favored at high temperatures and pressures, whereas at lower temperatures and pressures, isomerization and dealkylation of some lower alkyl aromatics take place.

As is known in the art, it is preferable to base exchange the crystalline aluminosilicate ZSM-12 with a source of hydrogen ions or ions capable of conversion thereto such as ammonium ions. It is known that these materials can also contain other desirable cations, such as rare earth cations, calcium ions, magnesium ions, as well as mixtures of the above.

As has previously been indicated, it is preferred that the zeolite ZSM-12 has associated therewith a hydrogenation/dehydrogenation component which is preferably platinum.

As is also known in the art, the zeolite ZSM-12 can be employed in combination with a support or binder material which acts as a diluent, for example, a porous inorganic support or a clay binder. Non limiting examples of such binder materials including alumina, zirconia, silica, magnesia, thoria, titania, and combinations thereof generally in the form of dried inorganic oxide gels and gelatinous precipitates. Suitable clay materials include by way of example, bentonite and kieselguhr. The relative proportions of suitable crystalline aluminosilicate ZSM-12 to the total composition of catalyst and binder may vary with the zeolite content ranging from about 10 to about 90 weight percent and usually within the range of about 20 to about 80 percent by weight of the composition. The amount of platinum which is associated with the crystalline aluminosilicate ZSM-12 is not narrowly critical and can range from about 0.1 to about 5 weight percent based on zeolite.

The novel process of this invention is applicable to both the total effluent from a methanol to gasoline process but its particular applicability resides in treating less than the total gasoline fraction since, quite obviously, the durene is concentrated at the higher boiling end and not at the light end. Accordingly, a particularly preferred embodiment of this invention resides in subjecting the total gasoline derived from the conversion of methanol to a distillation process or a fractionation process in order to remove at least the light olefinic fractions. The exact point at which the total gasoline is cut is not narrowly critical and a dividing point can be at temperatures ranging from about 200° to about 400° F. A more preferred cut point is from about 300° to 400° F. and more particularly preferred being at 350° F. The invention will be illustrated with respect to making an initial separation at 350° F., although it is to be understood that higher to lower temperatures can be used as set forth above. The 350°+ bottoms fractions from a conventional methanol to gasoline operation obtained by fractionating the liquid product is then dealkylated over ZSM-12 at the conditions of temperature and pressure and space velocity previously set forth.

The following examples will illustrate the best mode now contemplated for carrying out the invention.

EXAMPLES

The Feed

A 350° F. + bottoms cut from a methanol to gasoline process containing about 50% durene, 20% trimethylbenzenes (TMB), and 30% other $C_9+$ aromatics and which is a solid at room temperature was used for the examples which follow. The solid was dissolved in a minimum amount of trimethylbenzenes before charging into the unit such that the resulting feed contains about 58% trimethylbenzenes and 23% durene. In the examples which follow, the temperature and pressure of the unit were varied from 850°-900° F. and the pressure of the unit was varied from 100-400 psig, the hydrogen to hydrocarbon molar ratio and the weight hourly space velocity were kept constant at about 3.8 and 1.5 respectively. The platinum HZSM-12 catalyst was prepared by impregnation method so as to obtain 0.1% platinum based on weight of the total catalyst. The results obtained as well as additional operating parameters are shown in the following table.

TABLE

| | | Pt/HZSM-12 | | | |
|---|---|---|---|---|---|
| Example | | 1 | 2 | 3 | 4 |
| Temp., °F. | | 850 | 900 | 850 | 900 |
| Pressure, psig | | 400 | | 100 | |
| Time on Stream, hrs. | | 2.5 | 6.0 | 9.5 | 13.0 |
| ET Conv., wt. % | | 81.1 | 77.2 | 48.3 | 53.6 |
| TMB Conv., wt. % | | 42.2 | 50.9 | 13.1 | 11.5 |
| DEB Conv., wt. % | | 100.0 | 100.0 | 100.0 | 100.0 |
| EX Conv., wt. % | | 85.5 | 81.8 | 48.7 | 48.5 |
| Durene Conv., wt. % | | 83 | 86 | 62 | 63 |
| $C_{11}+$ Conv., wt. % | | 76.5 | 85.3 | 67.6 | 57.3 |
| Ring Loss, Mol % | | 6.3 | 7.5 | −0.6 | 1.1 |
| Prod. Dist., wt. % | Feed | | | | |
| $C_1$ | | 0.8 | 1.6 | 0.1 | 0.5 |
| $C_2$ | | 5.2 | 6.6 | 1.0 | 1.4 |
| $C_3$ | | 7.2 | 8.5 | 1.8 | 2.0 |
| $C_4-C_6$ | | 3.1 | 2.7 | 1.1 | 1.4 |
| Benzene | | 0.8 | 1.4 | 0.5 | 0.8 |
| Toluene | | 8.6 | 11.2 | 4.0 | 3.4 |
| Ethylbenzene | | 0.1 | 0.1 | 0.4 | 0.4 |
| Xylenes | 1.1 | 27.7 | 29.1 | 11.9 | 10.1 |
| Ethyltoluene | 2.4 | 0.4 | 0.5 | 1.2 | 1.1 |
| TMB | 57.8 | 33.2 | 28.1 | 50.2 | 51.1 |
| Diethylbenzene | 2.0 | 0.0 | 0.0 | 0.0 | 0.0 |
| Ethylxylene | 4.3 | 0.6 | 0.8 | 2.2 | 2.2 |
| Durene | 23.0 | 4.0 | 3.1 | 8.8 | 8.4 |
| $C_{10}+$ | 8.6 | 8.1 | 6.1 | 16.8 | 11.1 |
| Total | 99.3 | 100.0 | 100.0 | 100.0 | 100.0 |

As can be seen, durene conversion was directly related to both pressure and temperature in that the operations at 100 psi, i.e. Examples 3 and 4, had substantially lower durene conversion than those at 400 psi. The experiments also show that enhanced yields of benzene, toluene and xylenes are obtained at the higher pressures, i.e. Examples 1 and 2, than at the lower pressure, i.e. Examples 3 and 4.

What is claimed is:

1. In the process for the conversion of methanol to gasoline over a ZSM-5 type zeolite wherein methanol is contacted with said zeolite at elevated temperatures and pressures in order to effect conversion to liquid products including gasoline with a concurrent formation of durene and a portion of said liquid is contacted over a solid acidic catalyst, the improvement which comprises carrying out contact of a durene-containing fraction consisting essentially of $C_9+$ aromatics with zeolite ZSM-12 at a temperature within the range of 800° F. to 1050° F., a pressure within the range of 250 psig to 1000 psig, a hydrogen to hydrocarbon mol ratio greater than 1, and a space velocity of from 0.5 to 10 WHSV in order to dealkylate a substantial portion of the durene and enhance the yield of benzene, toluene and xylenes.

2. The process of claim 1 wherein said zeolite ZSM-12 has a hydrogenation/dehydrogenation metal associated therewith.

3. The process of claim 2 wherein said hydrogenation/dehydrogenation metal is platinum.

4. The process of claim 3 wherein said liquid fraction has a boiling point greater than about 300°–400° F. and contains at least about 23 wt.% durene.

5. The process of claim 3 wherein said liquid fraction has a boiling point greater than about 350° F.

* * * * *